(12) United States Patent
Contiliano et al.

(10) Patent No.: US 8,197,509 B2
(45) Date of Patent: Jun. 12, 2012

(54) SUTURE ANCHOR WITH IMPROVED TORSIONAL DRIVE HEAD

(75) Inventors: Joseph H. Contiliano, Somerville, NJ (US); Yufu Li, Bridgewater, NJ (US); Zhigang Li, Hillsborough, NJ (US); Nathan Cauldwell, Attleboro, MA (US)

(73) Assignee: DePuy Mitek, Inc., Raynham, MA (US)

( * ) Notice: Subject to any disclaimer, the term of this patent is extended or adjusted under 35 U.S.C. 154(b) by 1942 days.

(21) Appl. No.: 11/170,419

(22) Filed: Jun. 29, 2005

(65) Prior Publication Data
US 2007/0005069 A1 Jan. 4, 2007

(51) Int. Cl.
*A61B 17/04* (2006.01)
*A61F 5/00* (2006.01)
(52) U.S. Cl. .................. 606/232; 606/300; 606/301
(58) Field of Classification Search .................. 606/232, 606/73, 72, 281–321, 76, 77, 104, 86 A; 411/394, 411/398, 399, 402–405, 407, 408, 410, 419, 411/426; 81/52, 121.1, 124.1, 124.2, 437; 72/454; 279/148, 155
See application file for complete search history.

(56) References Cited

U.S. PATENT DOCUMENTS

| | | | |
|---|---|---|---|
| D248,014 S * | 5/1978 | DeCaro | D8/387 |
| 5,443,482 A | 8/1995 | Stone et al. | |
| 5,489,176 A * | 2/1996 | Fultz | 411/181 |
| 5,573,548 A | 11/1996 | Nazre et al. | |
| 5,814,070 A * | 9/1998 | Borzone et al. | 606/232 |
| 5,824,011 A | 10/1998 | Stone et al. | |
| 5,868,789 A | 2/1999 | Huebner | |
| 6,045,573 A | 4/2000 | Wenstrom, Jr. et al. | |
| 6,139,565 A | 10/2000 | Stone et al. | |
| 6,264,677 B1 * | 7/2001 | Simon et al. | 606/232 |
| 6,306,140 B1 * | 10/2001 | Siddiqui | 606/73 |
| 6,343,531 B2 | 2/2002 | Amis | |
| 6,368,322 B1 | 4/2002 | Luks et al. | |
| 6,610,080 B2 * | 8/2003 | Morgan | 606/232 |
| 2002/0052605 A1 | 5/2002 | Grooms et al. | |
| 2002/0120292 A1 * | 8/2002 | Morgan | 606/232 |
| 2002/0173822 A1 | 11/2002 | Justin et al. | |
| 2004/0082956 A1 | 4/2004 | Baldwin et al. | |
| 2004/0254580 A1 | 12/2004 | Boock et al. | |
| 2005/0090828 A1 | 4/2005 | Alford | |

FOREIGN PATENT DOCUMENTS
EP 0 686.373 A1 12/1995
* cited by examiner

*Primary Examiner* — Corrine M McDermott
*Assistant Examiner* — Jing Ou

(57) ABSTRACT

The present invention provides a suture anchor that includes an elongate shank defining a longitudinal axis and having at least one engaging member for applying the suture anchor within the bone and securing the suture anchor in the bone once implanted formed thereon, and a drive head having a proximal end, a distal end and a radial cross-sectional geometry, where the drive head is mated to the elongate shank, includes at least one suture attachment element formed in a portion thereof and at least one anti-rotational member integral therewith, suture anchor kits utilizing the suture anchors and methods of attaching bone to gone.

17 Claims, 8 Drawing Sheets

SUTURE ANCHOR WITH IMPROVED TORSIONAL DRIVE HEAD

FIELD OF THE INVENTION

The present invention relates to suture anchors having improved physical properties, more particularly, to biologically compatible suture anchors requiring torsional forces to secure their application within body tissue.

BACKGROUND OF THE INVENTION

Suture anchors are often used to attach a length of suture to bone in order to use the suture to secure detached soft tissue to the bone. Suture anchors typically have an anchor body, a suture attachment element, and a bone-engaging member for facilitating placement and retaining the suture anchor within bone. The anchor can be inserted into a preformed hole in the bone, and/or the anchor can be self-tapping and thus can include threads for securing the anchor within bone. Oftentimes suture anchors require the application of torsional forces from an insertion tool at one end of the anchor to drive the suture anchor into bone, as with screw-type anchors. Insertion tools are typically formed from an elongate shank having a mating element formed on a distal end thereof for mating with a corresponding mating element formed on or in the drive head of the fixation device. One common type of driver tool includes a hexagonal-shaped or square-shaped socket for receiving a corresponding hexagonal-shaped or square-shaped head of a suture anchor.

While conventional suture anchors and their drivers are sufficient, they have some drawbacks. Anchor heads with hexagonal or square shaped cross-sections, for example, tend to have a relatively low stripping strength, meaning that under relatively small torque loads the drive head is permanently damaged and torque transfer is thus inhibited. Additionally, this low stripping strength can be further reduced due to the structural integrity of the anchor head, whose drive interface has been compromised or weakened to some degree by the incorporation of a suture attachment element such as an eyelet used to attach the suture to the anchor head. If the head shape of an attachment element decreases the amount of material on the anchor drive head that interfaces with the driver, then the amount of material that needs to yield or be "stripped" from the drive head is reduced, thus reducing the stripping strength of the head.

Conventional suture anchor heads also tend to have a relatively low failure torque, which can result in shearing off of the drive head during insertion. This type of failure is also dependent upon the geometry of the head. In suture anchors, this failure may be exacerbated by the location of the suture attachment element in the head. In particular, if a loop is molded into and embedded within the anchor such that the loop extends outward from the head of the anchor to receive a suture, the entire drive head is relatively weakened and thus has the potential to shear off during insertion.

Suture anchors were historically constructed of implantable metals and alloys which afforded sufficiently high tensile and torsional strength to withstand the rigors of insertion, but the implant remained in the body for prolonged periods of time. Polymer, ceramic, or composite material systems, both biodegradable and non-biodegradable, have been developed for similar applications, but typically have lower tensile and torsional strength than metal counterparts, thus increasing the risk of device failure during application of high torque loads during insertion, as described above. More recently, biodegradable composite material systems have been developed that incorporate filler materials within the polymer matrix, such as calcium phosphate particles, which are osteoconductive. These filled systems may have further reduced tensile or torsional properties compared to unfilled polymer systems. Thus there is a need for an improved torsional drive head for suture anchors that have higher torsional resistance to strippage or shearing off.

One option to increase the failure torque of an anchor is to increase the size of the drive head. Large anchor heads, however, require a large driver tool, which in turn requires a relatively large tunnel to be formed in the bone. This is particularly undesirable, especially where the tunnel is to be formed in the cancellous bone, and where the procedure is minimally invasive and must traverse through a cannula or arthroscope. Accordingly, most suture anchors are adapted for use with a relatively small driver tool, and thus have relatively small drive heads which can result in a low failure torque and a low stripping strength, particularly in harder bone applications. A drive head of improved torsional strength is desirable to reduce the risk of deformation during insertion. Deformation may cause distortion of the anchor near the suture attachment regions, which can inhibit suture slideability necessary to afford knot tying. Additionally, a torsional drive head more resistant to deformation may make a revision procedure easier, as there are some instances where torque driven anchors need to be backed out and perhaps even reinserted.

Accordingly, there remains a need for suture anchors having improved physical properties, and in particular having a high failure torque and a high stripping strength.

SUMMARY

The present invention provides a suture anchor including an elongate shank that includes proximal and distal ends and defines a longitudinal axis. The shank further includes formed thereon at least one engaging member for facilitating placement of the suture anchor within the bone and securing the suture anchor in the bone once implanted. The suture anchor also includes a drive head having a proximal end, a distal end and a radial cross-sectional geometry; where the distal end is mated to the proximal end of the elongate shank. The drive head includes at least one suture attachment element formed in a portion thereof and at least one anti-rotational member integral therewith, which has a longitudinal cross-sectional geometry. The invention is also directed to suture anchor installation kits containing the suture anchor and a driver tool, as well as methods for attachment of soft tissue to bone.

BRIEF DESCRIPTION OF THE DRAWINGS

The invention will be more fully understood from the following detailed description taken in conjunction with the accompanying drawings.

DETAILED DESCRIPTION OF THE INVENTION

Figure 1A:
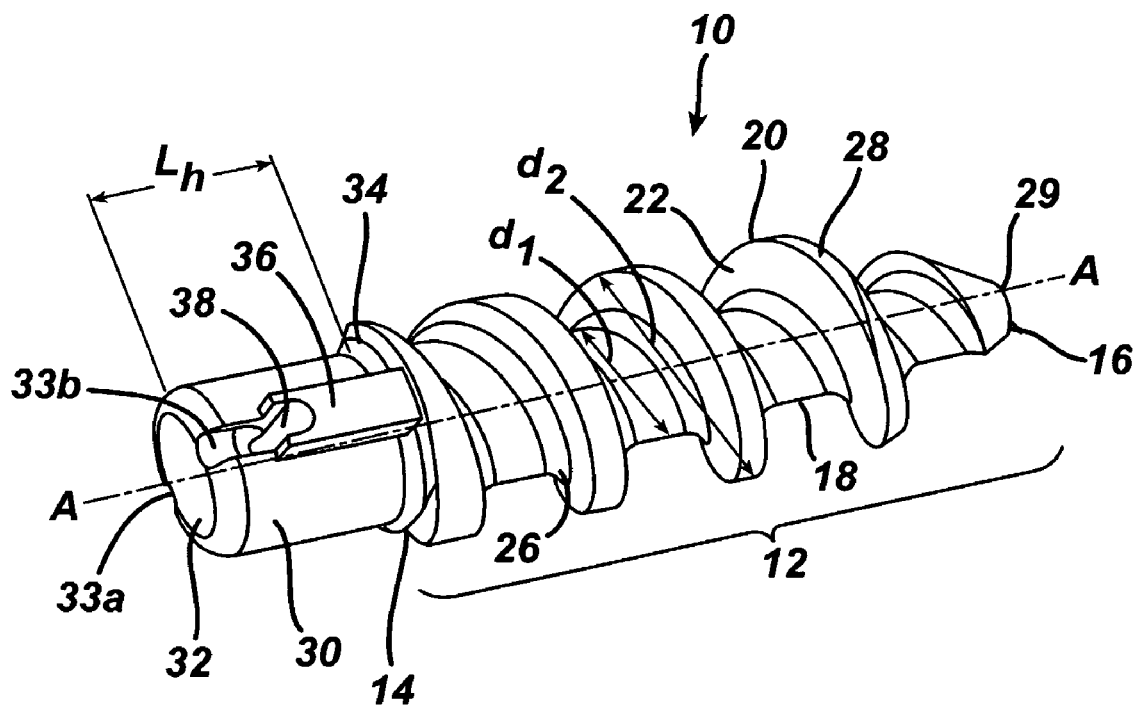
FIG. 1A is a perspective view of a suture anchor of the present invention.

The present invention provides a suture anchor including an elongate shank defining a longitudinal axis and having at least one engaging member formed therewith to engage bone and facilitate placement of the suture anchor within the bone and to secure the suture anchor in the bone once implanted. The suture anchor also includes a drive head for applying torsion to the elongate shank having a proximal end and a distal end and which is mated to the elongate shank so as to transfer the torsion to the elongate shank, thereby providing for placement of the suture anchor within the bone. The drive head may have a circular or a substantially non-circular radial cross-sectional geometry, for example an oval, and includes at least one anti-rotational member (ARM) formed integral therewith to provide for improved transfer of the torsion to the shank, and a suture attachment element formed in a portion of the drive head for attaching a suture to the suture anchor. As used herein, member is meant to include a structural unit of the shank and/or drive head, respectively, each of which forms a part of the suture anchor. As used herein, element is meant to include a constituent of the drive head for receiving a suture, for example a suture tunnel and/or suture channel.

In one embodiment, the suture attachment element comprises a suture tunnel extending through the drive head, either substantially transversely or such that the suture tunnel intersects the longitudinal axis of the suture anchor. The suture tunnel is of sufficient diameter so as to allow a suture of a selected size to pass there through. The suture is passed through the tunnel and looped through such that both suture ends (either with or without a needle) point in the same direction and can then be loaded onto the suture anchor driver. The suture attachment element can also include a longitudinally oriented suture-receiving channel in cooperation with the suture tunnel formed on an outer surface of the drive head. In one embodiment, the suture tunnel is formed proximal to the distal end of the drive head to present a channel-free portion in the drive head. The channel-free portion provides additional structural integrity to the drive head of the suture anchor to minimize the risk of shearing during insertion. In another embodiment, the drive head includes a first suture tunnel having a first pair of opposed suture-receiving channels extending proximally there from, and a second suture tunnel having a second pair of opposed suture-receiving channels extending proximally there from.

In one embodiment the suture anchor comprises a drive head of circular or substantially non-circular radial cross-sectional geometry with at least one ARM integral therewith. In a second embodiment, the suture anchor comprises a drive head of circular or substantially non-circular radial cross-sectional geometry with multiple ARMs located on either side of a plane of symmetry for ease of inserter application. The ARMs are of configuration and dimension effective to provide a mating fit with the driver tool in order to ensure efficient transfer of torsion from the drive head to the shank. The presence of the ARMs provides high failure torque and high stripping strength.

In other aspects, a suture anchor and installation kit is provided, including at least one suture anchor and a cylindrical driver tool for cooperating with the suture anchor. The suture anchor has a shank with an engaging member formed thereon and defining a longitudinal axis. A drive head is formed on the shank and has a circular or substantially non-circular radial cross-sectional geometry, such as oval, and at least one ARM formed integral therewith. The cylindrical driver tool has a distal end with a socket formed therein having a shape adapted to receive and engage the drive head of the anchor in a mating relationship. The ARM(s) also provide positive mating with the driver tool, such as a key in keyway configuration, to reduce driver slip-off, especially during off-angle insertions. In an exemplary embodiment, the driver tool has an outer diameter that is equal to or less than an outer-most diameter of the engaging member of the anchor.

As shown in FIGS. 1A-1E, where like numbers refer to like features, the present invention generally provides suture anchor 10, including elongate shank 12 defining longitudinal axis A and having at least one engaging member 20 formed thereon. In the embodiment shown, engaging member 20 is a helical thread. Drive head 30 has proximal end 32 and distal end 34 mated to elongate shank 12 at proximal end 14. Drive head 30 has a an oval radial cross-sectional geometry, though drive head 30 could have a substantially circular, rectangular, square, hexagonal, or flattened oval radial cross-sectional geometry, and includes at least one suture attachment element 38 formed therein. The radial cross-section is defined as the cross-section perpendicular to longitudinal axis A. Generally, oval is known to include flattened ovals and ovals with flat portions perpendicular to the major $X_2$ or minor $X_1$ diameters of drive head 30. In an exemplary embodiment, minor diameter $X_1$ of drive head 30 is about three-fourths the size of major diameter $X_2$, and major diameter $X_2$ of drive head 30 is equal to or less than minor diameter $d_1$ of shank 12.

The configuration of drive head 30 includes at least one ARM 36 protruding from and integral with drive head 30 and extending from distal end 34 towards proximal end 32 of drive head 30. Additionally, drive head 30 contains at least one suture tunnel 38 and further contains suture-receiving channels 33a and 33b. ARM 36 is shown here in the plane of suture tunnel 38, although those skilled in the art, once having the benefit of this disclosure, will realize that ARM 36 and suture tunnel 38 need not align with one another. It may be desirable for such an alignment of ARM 36 with suture tunnel 38 to occur to further strengthen the suture tunnel region, although this is not necessary within the scope of the invention. The configuration of drive head 30 with ARM 36 is particularly advantageous in that it provides suture anchor 10 with improved physical properties, including a high failure torque and high stripping strength.

Elongate shank 12 of suture anchor 10 can have a variety of configurations and can include a variety of engaging members 20 formed thereon. FIG. 1A illustrates an exemplary embodiment of suture anchor 10 having shank 12 including core 18 with single helical thread 20 extending around core 18 from proximal end 14 to distal end 16 of shank 12. Thread 20 includes proximal and distal facing flanks 22 and 24, respectively, that extend between base 26 and substantially flattened crest 28. Thread 20 defines major diameter $d_2$ of shank 12, which can vary along the length of shank 12, although major diameter $d_2$ is substantially constant along a substantial portion of shank 12. Threads 20, however, can taper at the distal portion of shank 12 to terminate at apex 29 of shank 12. Core 18 of shank 12 defines minor diameter $d_1$ that can also be substantially constant, or can vary along the length of shank 12. As shown in FIG. 1A, core 18 tapers from proximal end 14 to distal end 16. Once having the benefit of this disclosure, one skilled in the art will appreciate that shank 12 shown in FIG. 1A is merely an exemplary embodiment of shank 12, and that a variety of shanks having different tissue-engaging members can be used with suture anchor 10 in accordance with the present invention.

Figure 1B:
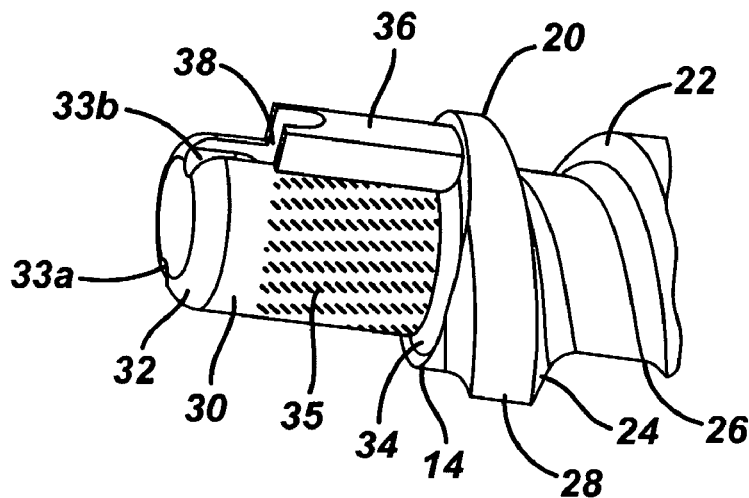
FIG. 1B is another perspective view of the suture anchor shown in FIG. 1A.
Figure 1C:
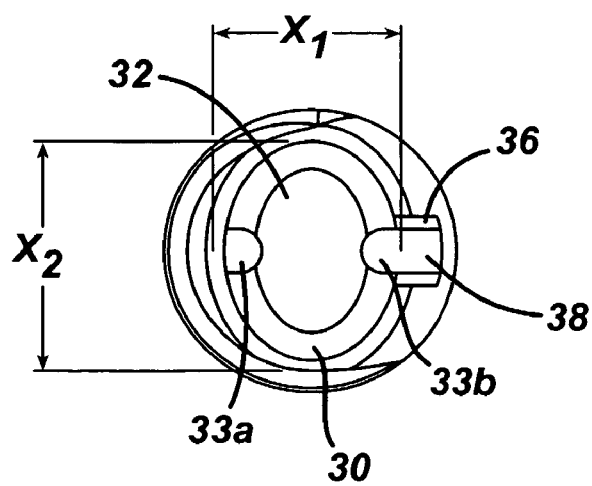
FIG. 1C is top view of the suture anchor shown in FIG. 1A.

Drive head 30 of suture anchor 10 is shown in more detail in FIGS. 1B and 1C, and is attached to, or formed integrally with, shank 12. The relatively small size of major diameter $X_2$ of drive head 30, as compared to major diameter $d_2$ of shank 12, is particularly desirable so that drive head 30 will not require a larger tunnel to be formed in the bone than is necessary. Drive head 30 further includes length $L_h$ (shown in FIG. 1A) that extends between proximal and distal ends 32 and 34 thereof. Length $L_h$ of drive head 30 can vary, although length $L_h$ of drive head 30 may be optimized to allow the drive head to be received within a driver tool and to be driven into bone without shearing off. Drive head 30 has ARM 36 extending along length $L_h$ between distal end 34 of drive head 30 and the opening of suture tunnel 38.

While a variety of suture attachment elements can be used, FIGS. 1A-1E illustrate an exemplary embodiment of suture anchor 10 having suture tunnel 38 that extends through drive head 30 and that allows a length of suture to be disposed there through. Suture tunnel 38 may terminate at a position proximal to distal end 32 of drive head 30 to provide channel-free portion 35 in drive head 30. Since distal portion 34 of anchor head 30 is typically the part of anchor 10 that is under the most stress during insertion, channel-free portion 35 (shown as shaded area) provides a much stronger, more dense portion of drive head 30 that will minimize the risk of shearing during insertion.

Suture anchor 10 can also optionally include longitudinally oriented suture-receiving grooves or channels 33a and 33b formed therein. Suture-receiving channels 33a and 33b are formed in the outer surface of drive head 30 and may be spaced equidistant from one another. As shown in FIG. 1C, two opposed suture-receiving channels 33a and 33b are positioned along minor diameter $X_1$ of drive head 30.

Figure 1D:
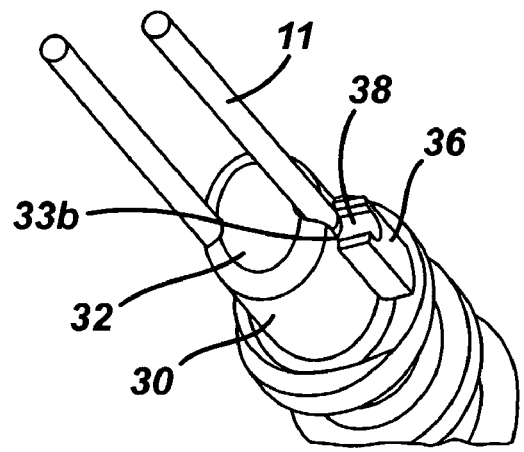
FIG. 1D is another perspective view of a suture anchor of the present invention, showing a suture in place.
Figure 1E:
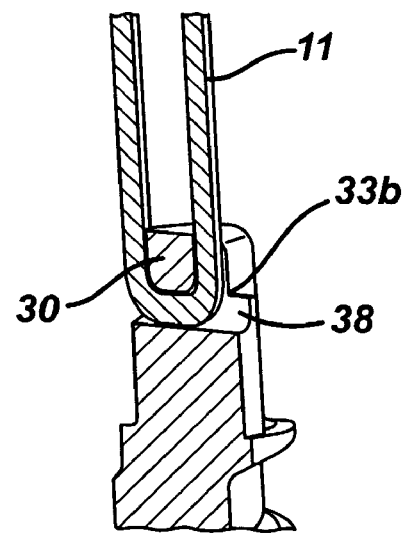
FIG. 1E is a cross sectional view of the drive head portion of a suture anchor of the present invention with a suture in place.

FIGS. 1D and 1E show drive head 30 of the present invention with ARM 36 and suture 11. Suture 11 is shown passing through drive head 30 by means of suture tunnel 38. A longitudinal cross-sectional view of drive head 30 with suture 11 passing through suture tunnel 38 and along suture-receiving channels 33a and 33b is shown in FIG. 1E.

Figure 2:
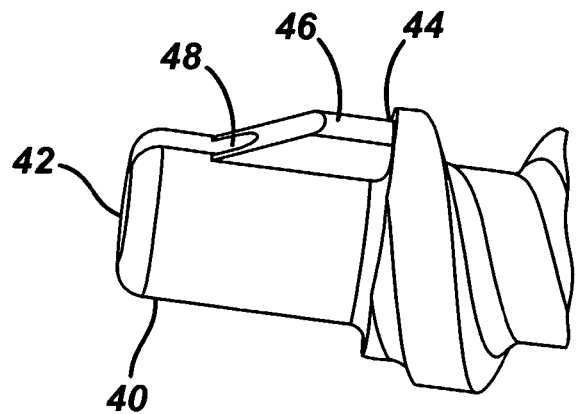
FIG. 2 is a perspective view of an alternate embodiment of the drive head portion of a suture anchor of the present invention.

FIG. 2 shows an alternate embodiment of drive head 40 of a suture anchor according to the present invention. In this embodiment, the radial cross-sectional geometry of drive head 40 is substantially oval in shape with ARM 46 thereon that originates at distal end 44 and extends to the opening of suture tunnel 48. As shown, ARM 46 is tapered from suture tunnel 48 towards distal end 44. Once having the benefit of this disclosure, those skilled in the art will recognize that ARM 46 may be of other longitudinal cross-sectional geometries, e.g. parabolic, wedge, etc., without deviating from the scope of the invention, and that the ARM may extend only partially from distal end 44 toward proximal end 42. Additionally, ARM 46 may taper in the opposite orientation, i.e. from distal end 44 towards proximal end 42.

In alternate embodiments, the suture anchor of the present invention may have multiple suture tunnels extending transversely through the anchor, preferably at different positions along the longitudinal axis of the suture anchor so that they would not intersect one another. These suture tunnels may be located in the drive head of the suture anchor and affect the structural integrity of the drive head.

Figure 3:
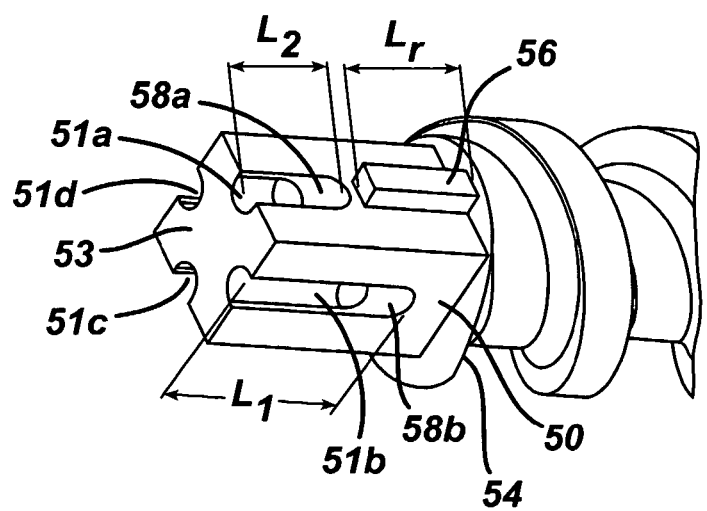
FIG. 3 is a perspective view of an alternate embodiment of the drive head portion of a suture anchor of the present invention.

As shown in FIG. 3, suture tunnels 58a and 58b and suture-receiving channels 51a, 51b, 51c, and 51d may be positioned along the longitudinal axis of drive head 50. The position of suture-receiving channels 51a, 51b, 51c, and 51d can also vary, in one embodiment extending through proximal end 53 of drive head 50 and terminate at an opening of the corresponding suture tunnel. For example, suture-receiving channels 51a and 51c correspond to suture tunnel 58a and suture-receiving channels 51b and 51d correspond to suture tunnel 58b. Where the suture tunnels are positioned proximal to distal end 54 of drive head 50, suture-receiving channels 51a, 51b, 51c, and 51d can also terminate at a position proximal to distal end 54 of drive head 50 to provide a channel-free portion similar to that shown in FIG. 1B in the head 30. Moreover, where two suture tunnels are provided at locations along the length of the drive head 50, a first pair of opposed suture-receiving channels, e.g., suture-receiving channels 51b and 51d, can have a length $L_1$ that is equal to or different than a length $L_2$ of a second pair of opposed suture- receiving channels, e.g., suture-receiving channels 51a and 51c. However channels 51a, 51b, 51c, and 51d must have lengths less than $L_h$. In this embodiment, drive head 50 contains ARM 56 thereon. ARM 56 originates at distal end 54 of drive head 50 and terminates at the opening of suture tunnel 58a.

In FIG. 3, only one ARM 56 is shown. However, there may be a plurality of ARMs spaced equidistant around the drive head. Multiple ARMs (not shown) may be desirable from a procedural standpoint where the non-circular head geometry possesses a plane of symmetry. In the embodiment shown in FIG. 3, the square drive head has two planes of symmetry. With ARMs on either side of a plane of symmetry, rotational alignment of the mating inserter (shown in FIGS. 8A-9B) with respect to the implant is further alleviated. Multiple ARMs may also afford further improved physical properties. Once having the benefit of this disclosure, those skilled in the art will recognize other possible configurations with multiple ARMS on either side of a plane of symmetry keeping within the scope of the invention.

Figure 4:
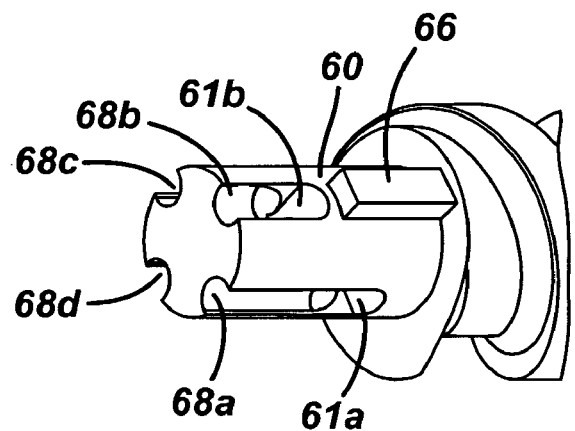
FIG. 4 is a perspective view of an alternate embodiment of the drive head portion of a suture anchor of the present invention.
Figure 5:
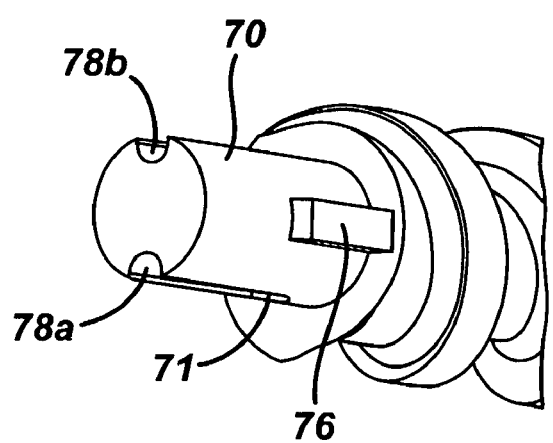
FIG. 5 is a perspective view of an alternate embodiment of the drive head portion of a suture anchor of the present invention.

In FIG. 4, an alternate embodiment of drive head 60 is shown. Drive head 60 is circular in radial cross-section and contains ARM 66, two suture tunnels 61a and 61b and suture-receiving channels 68a, 68b, 68c, and 68d, where ARM 66 is aligned with suture-receiving channels 68b and 68d. FIG. 5 shows another alternate embodiment of drive head 70. This embodiment contains ARM 76, suture tunnel 71 and suture-receiving channels 78a and 78b, where ARM 76 is not aligned with suture tunnel 71.

Figure 6:
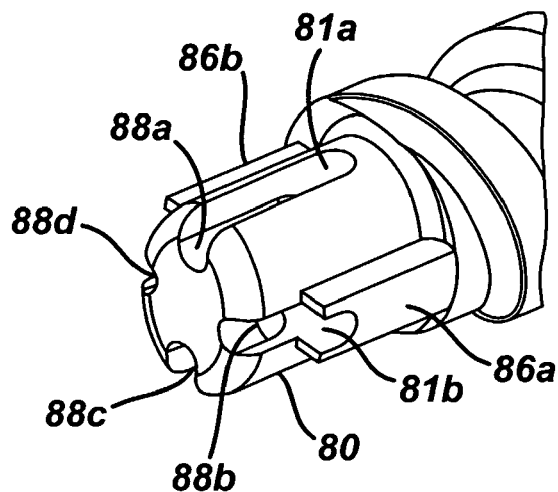
FIG. 6 is a perspective view of an alternate embodiment of the drive head portion of a suture anchor of the present invention.
Figure 7:
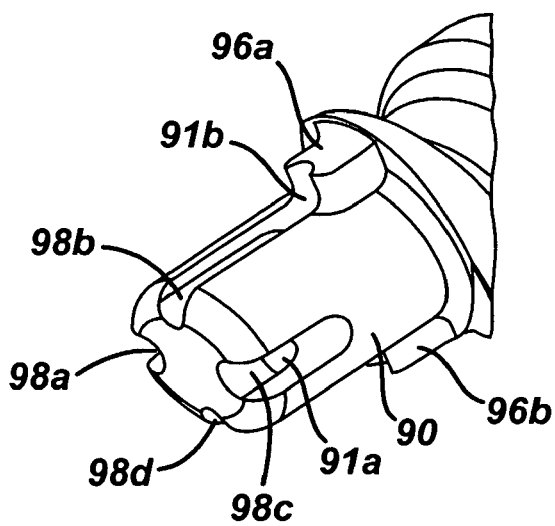
FIG. 7 is a perspective view of an alternate embodiment of the drive head portion of a suture anchor of the present invention.

FIG. 6 shows an exemplary embodiment of drive head 80 of suture anchors of the present invention where drive head 80 is substantially oval in radial cross-section and has two ARMs 86a and 86b, two suture tunnels 81a and 81b and four suture-receiving channels 88a, 88b, 88c, and 88d. FIG. 7 shows an exemplary embodiment of drive head 90 of suture anchors of the present invention where drive head 90 and two ARMs 96a and 96b, two suture tunnels 98a and 98b and four suture receiving channels 91a, 91b, 91c, and 91d. FIG. 6 shows an embodiment where ARMs 86a and 86b are oriented with the more proximally placed suture tunnel 81b and suture-receiving channels 88b and 88d, while FIG. 7 shows the opposing embodiment where ARMs 96a and 96b are oriented with the more distally placed suture tunnel 98b and suture-receiving channels 91b and 91d.

Figure 8A:
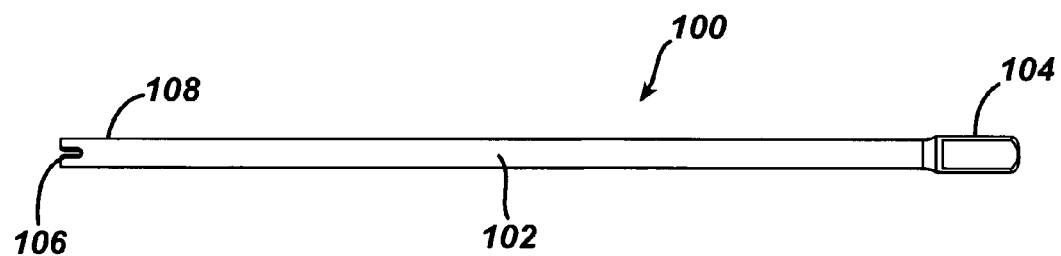
FIG. 8A is a side view of one embodiment of a driver tool in accordance with the present invention.
Figure 8B:
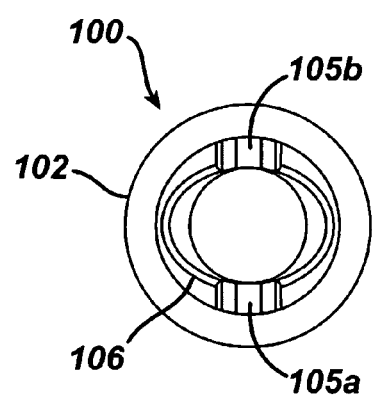
FIG. 8B is an end view of the distal-most end of the driver tool shown in FIG. 8A.
Figure 9A:
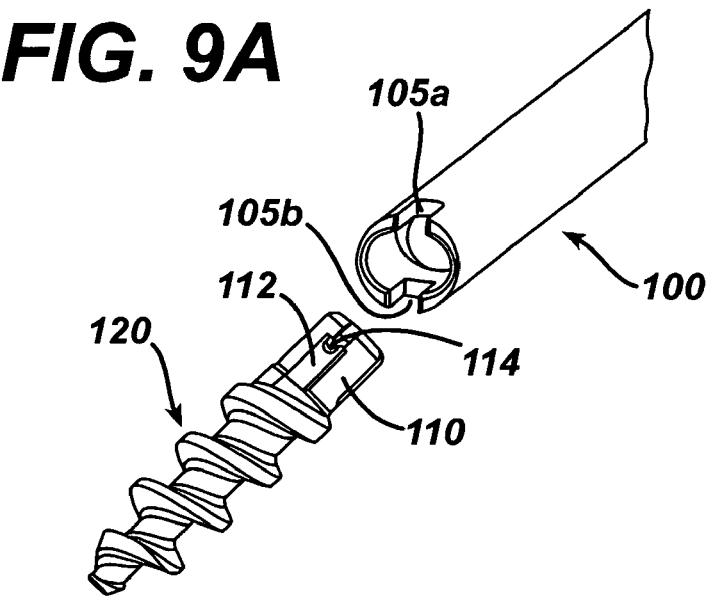
FIG. 9A is a perspective view of one embodiment of a suture anchor and driver tool where the head of the driver is not mated with the socket of the driver tool.
Figure 9B:
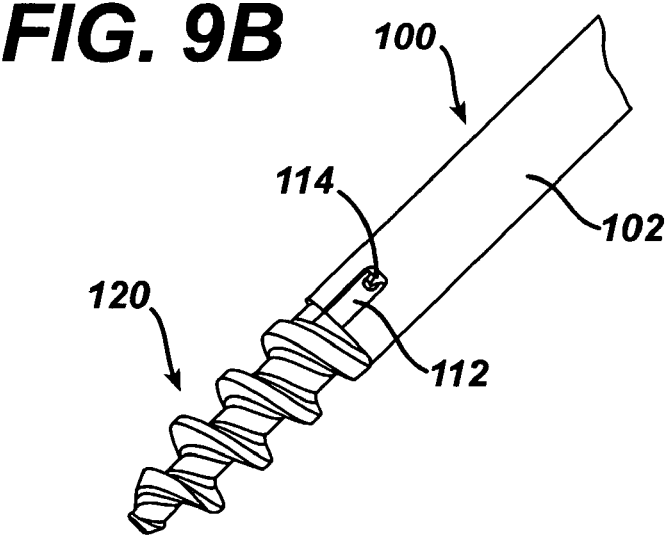
FIG. 9B is a perspective view of one embodiment of a suture anchor and driver tool of the present invention.

For placement of suture anchors of the present invention into bone, suture anchors can be driven into bone using a driver tool, such as shown in FIGS. 8A-8B. Driver tool 100 can have a variety of shapes and sizes, but typically includes 10 elongate shaft 102 having proximal handle portion 104 and distal end 108 having socket 106 formed therein and adapted to seat in mating relationship with the drive head of suture anchors of the present invention. As shown in FIGS. 8A-8B, socket 106 of driver tool 100 has an overall oval shape and includes opposed ARM-engaging elements 105a and 105b to engage and cooperate with ARM(s) 112 once the drive head of the suture anchor is placed in cooperation with socket 106 of driver tool 100. The shape of socket 106 and ARM-engaging elements 105a and 105b form a close fit with oval-shaped drive head 110 and cooperate with ARM(s) 112 of in such a way as to provide the mated relationship of the drive head within the socket. The size and configuration of the socket in relationship to the drive head and ARMs should be sufficient to provide a secure fit between the drive head and the driver tool, and to prevent rotation of the driver tool with respect to the suture anchor. Driver tool 100 can also contain an inner lumen (not shown) extending there through for receiving free ends of suture.

Suitable materials from which suture anchors of the present invention may be formed include biocompatible polymers selected from the group consisting of aliphatic polyesters, polyorthoesters, polyanhydrides, polycarbonates, polyurethanes, polyamides and polyalkylene oxides. The present invention also can be formed from biocompatible metals, glasses or ceramics, or from autograft, allograft, or xenograft bone tissues. Suture anchors can be further comprised of combinations of metals, ceramics, glasses and polymers.

The biocompatible materials can be biodegradable or non-biodegradable. Biodegradable materials, such as polymers, readily break down into small segments when exposed to moist body tissue. The segments then either are absorbed by the body, or passed by the body. More particularly, the biodegraded segments do not elicit permanent chronic foreign body reaction, because they are absorbed by the body or passed from the body, such that the body retains no permanent trace or residue of the segment.

In one embodiment, the suture anchor comprises biodegradable aliphatic polymer and copolymer polyesters and blends thereof. The aliphatic polyesters are typically synthesized in a ring opening polymerization. Suitable monomers include but are not limited to lactic acid, lactide (including L-, D-, meso and D, L mixtures), glycolic acid, glycolide, epsilon-caprolactone, p-dioxanone (1,4-dioxan-2-one), and trimethylene carbonate (1,3-dioxan-2-one).

In another embodiment, the materials comprising the devices will be biodegradable glasses or ceramics comprising mono-, di-, tri-, alpha-tri-, beta-tri-, and tetra-calcium phosphate, hydroxyapatite, calcium sulfates, calcium oxides, calcium carbonates, magnesium calcium phosphates, phospate glasses, bioglasses, and mixtures thereof.

In another embodiment, the materials comprising the devices can be combinations of biodegradable ceramics and polymers. Composites are prepared by incorporating biodegradable ceramic reinforcements such as fibers, short-fibers, or particles in a biodegradable polymer matrix.

Some particularly useful composites are 30 weight percent beta-tricalcium phosphate particles in 70 weight percent poly (lactic acid), or 30/70 beta-TCP/PLA, and 30 weight percent beta-tricalcium phosphate particles in 70 weight percent poly (lactide)/poly(glycolide) copolymer (mole ratio lactide to glycolyde 85/15), or 30/70 beta-TCP/(85/15 PLGA).

In another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. Therapeutic agents which may be administered via the pharmaceutical compositions of the invention include growth factors, including bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-beta I-III), vascular endothelial growth factor (VEGF); and other naturally derived or genetically engineered proteins, polysaccharides, glycoproteins, or lipoproteins.

Matrix materials for the present invention may be formulated by mixing one or more therapeutic agents with the polymer. Alternatively, a therapeutic agent could be coated on to the polymer, maybe with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

Methods for using a suture anchor in accordance with the present invention are also provided. In methods for attaching soft tissue to bone according to the present invention, a cavity of sufficient size to receive suture anchors of the present invention may be formed within a bony structure. A suture anchor according to the present invention comprising a suture disposed within the suture attachment element is then attached to a driver tool as shown herein above, and inserted into the bone cavity via the driver tool. In certain embodiments the suture anchor may be placed directly into the bony structure without the need for pre-formation of the cavity. The driver tool is removed and the soft tissue in proximity to the suture anchor is attached to the suture anchor via the suture.

The following examples are illustrative of the principles and practice of the present invention, although not limited thereto.

EXAMPLE 1

Insertion Torque to Failure Tests

Suture anchors with the drive head of the design in FIG. 7 consisting of two ARM's, each approximately 0.050" in height and width, aligned in the plane of the suture eyelets, were subjected to insertion torque to failure tests versus a similar design without the two ARMs. Anchors were machined out of polysulfone.

Torque to failure tests were conducted in solid rigid polyurethane foam blocks (Sawbones, 1522-02, Pacific Research Laboratories, Inc., Vashon, Wash.). Torque measurements were recorded in inch-pounds using an Imada (Imada, Inc., Northbrook, Ill.) model DSD-4 Digitial Torque Tester/Screwdriver with mating ¼" hexagonal drive Jacobs chuck attachment. The mean torque to failure of five anchors with ARMs was 7.0 in-lbs compared to 5.6 in-lbs for anchors designs without ARM's, representing a 25% increase in torque capacity of the drive head due to the present invention (ARM's) in polysulfone.

EXAMPLE 2

Insertion Torque to Failure Tests

Suture anchors with the drive head of the design in FIG. 6 consisting of two ARM's, each approximately 0.125" in height and 0.050" in width, aligned in the plane of the suture eyelets, were subjected to insertion torque to failure tests versus a similar design without the two ARMs and with the eyelets reversed, thus having the most distal eyelet traverse the long axis of the oval head while the proximal eyelet traverses the short axis of the oval head. Anchors were injection molded from a 30/70 by weight beta-TCP/(85/15 poly(lactide)/poly(glycolide) composite material (starting Inherent Viscosity of raw polymer approximately 3.0 dl/g measured in chloroform (CHCl3) using the Cannon Automated Viscometer).

Torque to failure tests were conducted in solid rigid polyurethane foam blocks (Sawbones, 1522-02, Pacific Research Laboratories, Inc., Vashon, Wash.) under approximately a 6-10 lb compressive load. Torque measurements were recorded in inch-pounds using an Imada (Imada, Inc., Northbrook, Ill.) model DSD-4 Digitial Torque Tester/Screwdriver with mating ¼" hexagonal drive Jacobs chuck attachment. The mean torque to failure of five anchors with ARMs was 7.8 in-lbs compared to 5.9 in-lbs for anchors designs without ARM's, representing a 32% increase in torque capacity of the drive head due to the present invention (ARM's) in the molded composite material.

What is claimed is:

1. A suture anchor, comprising:
    an elongate shank comprising a proximal end and a distal end and defining a longitudinal axis, said shank further comprising at least one engaging member formed thereon; and
    a drive head comprising a proximal end, a distal end, a radial cross-sectional geometry, at least one suture attachment element formed in a portion thereof, and at least one anti-rotational member comprising a longitudinal cross-sectional geometry protruding from and integral with said drive head, wherein said drive head is mated to said elongate shank.

2. The suture anchor of claim 1 wherein said elongate shank tapers from said proximal end to said distal end.

3. The suture anchor of claim 1 wherein said at least one engaging member comprises a helical thread.

4. The suture anchor of claim 1 wherein said radial cross-sectional geometry of said drive head is non-circular.

5. The suture anchor of claim 4 wherein said radial cross-sectional geometry of said drive head is rectangular, square, hexagonal, flattened oval or oval.

6. The suture anchor of claim 5 wherein said radial cross-sectional geometry of said drive head is oval.

7. The suture anchor of claim 1 wherein said anti-rotational member extends between the distal end of the drive head and the suture attachment element.

8. The suture anchor of claim 1 wherein said anti-rotational member is tapered proximally along the length of the drive head.

9. The suture anchor of claim 1 wherein an even number of said anti-rotational members are symmetrically disposed on said drive head about a plane of symmetry of said drive head.

10. The suture anchor of claim 1 wherein said longitudinal cross-sectional geometry of said anti-rotational member is rectangular, curved, parabolic, or triangular.

11. The suture anchor of claim 1 wherein said suture attachment element comprises at least one suture tunnel extending transversely through said drive head.

12. The suture anchor of claim 1 wherein said drive head further comprises at least one suture-receiving channel formed in an outer surface of said drive head and originating at and extending proximally from an opening of said suture tunnel.

13. The suture anchor of claim 1 wherein said anchor comprises a biodegradable material.

14. The suture anchor of claim 13 wherein said biodegradable material is a polymer, copolymer, or polymer blend formed from monomers selected from the group consisting of lactic acid, lactide, glycolic acid, glycolide, epsilon-caprolactone, 1,4-dioxan-2-one and 1,3-dioxan-2-one.

15. The suture anchor of claim 13 wherein said biodegradable material is selected from the group consisting of biodegradable glass, mono-calcium phosphate, dicalcium phosphate, tricalcium phosphate, alpha-tricalcium phosphate, beta-tricalcium phosphate, tetracalcium phosphate, hydroxyapatite, calcium sulfate, calcium oxide, calcium carbonate, magnesium calcium phosphate, phospate glass and bioglass.

16. The suture anchor of claim 13 wherein said biodegradable material is a composite comprised of beta-tricalcium phosphate and poly(lactide).

17. The suture anchor of claim 13 wherein said biodegradable material is a composite comprised of 30 weight percent beta-tricalcium phosphate particles in 70 weight percent poly(lactide)/poly(glycolide) copolymer, wherein the mole ratio of lactide to glycolyde is 85/15.

* * * * *